United States Patent [19]

Strojny

[11] 4,328,373

[45] May 4, 1982

[54] METHOD OF PREPARING ALDEHYDES

[75] Inventor: Edwin J. Strojny, Midland, Mich.

[73] Assignee: The Dow Chemical Company, Midland, Mich.

[21] Appl. No.: 130,755

[22] Filed: Mar. 17, 1980

[51] Int. Cl.³ ............................................. C07C 45/41
[52] U.S. Cl. .................................. 568/435; 568/420; 568/484
[58] Field of Search ................ 568/435, 465, 420, 484

[56] References Cited

U.S. PATENT DOCUMENTS 1,966,067  7/1934  Jaeger ................................. 568/435
2,018,350  10/1935  Drossbach et al. .................. 568/435
2,105,540  1/1938  Lazier ................................. 568/484
4,093,661  6/1978  Trecker et al. .................. 568/435 X

OTHER PUBLICATIONS

Wagner et al, Synthetic Org. Chem., p. 294.

Primary Examiner—Bernard Helfin
Attorney, Agent, or Firm—Douglas N. Deline

[57] ABSTRACT

An improved vapor phase process for producing aldehydes from corresponding carboxylic acids and esters of said carboxylic acids by contacting the acid or ester at temperatures from about 300° C. to about 500° C. with hydrogen, in the presence of a catalyst selected from certain metal oxides.

7 Claims, No Drawings

METHOD OF PREPARING ALDEHYDES

BACKGROUND OF THE INVENTION

This invention relates to an economical process for the direct reduction of organic carboxylic acids and esters derived from said acids to the corresponding aldehydes.

U.S. Pat. Nos. 3,935,265 describes a method for the direct reduction of aromatic esters to aromatic aldehydes by contacting the ester with alumina at a temperature from about 400° C. to about 500° C. and at ambient pressure. Contact time can be as low as about three seconds. The best conversion using methyl benzoate ester was 39 percent, providing selectivity to benzaldehyde of 37 percent. The reference teaches that combinations of alumina and transition metals such as chromia-alumina may also be acceptable.

Other known catalysts for benzoic acid hydrogenation by gaseous hydrogen include a copper/chromium-containing substance made by co-precipitating copper, chromium and manganese salts and pelletizing the resulting product with diatomaceous earth and $CrO_3$ (Japan Kokai 75 111,034). Alkali metal oxides and zinc oxide catalysts have also been disclosed. p It is also known to treat alumina-containing catalysts at elevated temperatures of up to 1000° C. in order to improve their selectivity towards production of aldehyde product.

SUMMARY OF THE INVENTION

This invention relates to a novel method of producing aldehydes from organic carboxylic acids and esters of said acids by the vapor phase catalytic reduction of said compounds in the presence of hydrogen. More specifically, the invention relates to novel catalysts for use in the above-described process. These novel catalysts include oxides of certain metals including yttrium, zirconium, the lanthanides and actinides or a mixture thereof. Preferred are oxides of yttrium, zirconium, cerium, praseodymium, thorium and uranium. Most preferred are yttrium and zirconium oxide.

The catalysts of the invention provide greater conversion and more importantly greater selectivity to aldehyde production with only minor amounts of by-product formation than previously known catalysts.

DETAILED DESCRIPTION OF THE INVENTION

The carboxylic acids and esters of carboxylic acids capable of utilization according to the instant invention are extremely varied. Included are both $C_{1-12}$ monocarboxylic and dicarboxylic acids, the latter suitably being reduced to the corresponding dialdehydes. Esters include phenyl and $C_{1-6}$ alkyl esters of the above carboxylic acids.

Aliphatic carboxylic acids are those having at most only one α hydrogen. Preferably such compounds are devoid of α hydrogens. Examples include di- and trialkyl-substituted acetic acids.

Aromatic carboxylic acids include benzoic, phthalic and terephthalic acid and such acids further substituted with one or more ring substituents which are substantially inert under the conditions encountered during the vapor phase catalytic reduction reaction, for example alkyl, alkoxy, hydroxy or halogen substituents.

Preferred are benzoic and alkyl- or halo-substituted benzoic acids, di- and trialkyl-substituted acetic acids and phenyl or $C_{1-6}$ alkyl esters thereof. Most preferred are benzoic acid and $C_{1-6}$ alkyl esters thereof.

The catalysts for use according to this invention are produced by roasting the desired metal salt at temperatures up to about 600° C. under oxidizing conditions. The compounds are thereby converted to the corresponding metal oxides. The catalyst may then be compressed into pellets in order to facilitate handling and increase the catalyst density and structural integrity. Optionally, the metallic salts may be first deposited onto an inert supportive means and the resulting structure heated as before to produce a supported metal oxide catalyst. This technique is already known in the art. Accordingly the corresponding water-soluble salt of the metal is dissolved in water and inert supportive material such as $Al_2O_3$ in, for example, pellet form may be added. Preferred water-soluble salts are the nitrate salts. The resulting mixture is heated to evaporate water until the catalyst appears to be substantially dehydrated. At this point the catalyst may be roasted at a higher temperature to form the corresponding supported metallic oxide catalyst or alternatively the dehydrated catalyst may be first treated with ammonium hydroxide to form the metallic hydroxide which may then be roasted as before described.

In using the catalysts of this invention to reduce acids to aldehydes either a batch mode or continuous flow system may be employed. A continuous flow system wherein products are continuously removed, fresh reactants are continuously added and by-products or unreacted reactants are continuously removed or alternatively recycled is preferably employed.

The temperature of the reduction reaction should be maintained between about 300° C. and about 500° C.; preferably, from about 350° C. to about 450° C. Below 300° C. conversion is found to be too low, while above 500° C. excessive carbonization occurs.

The catalyst is packed into a suitable reactor vessel constructed from materials known to be stable at the operating conditions employed. Suitable materials include steel, stainless steel, glass, titanium, etc. A purge of inert gas such as dry nitrogen may be first used to clear undesirable foreign compounds from the reaction vessel prior to introduction of reactants.

Pressure may be varied over wide operating limits from subatmospheric to superatmospheric; however, it is preferred not to operate at reduced or extremely elevated pressures in order to avoid expensive systems designed to operate at these pressure extremes. Most preferred operating pressures are from about one atmosphere to about 2 atmospheres pressure.

Hydrogen is introduced into the reactor through a gas inlet. The hydrogen comprises a carrier stream which is passed through the catalyst bed of the reactor and optionally recovered and recycled through the reactor. The carboxyl-containing reactant may be added to the hydrogen stream and the mixture passed through the reactor. Recovery and recycle of unreacted carboxyl-containing reactant may also be employed. Hydrogen is preferably added in a stoichiometric excess. Molar ratios of hydrogen to carboxylic reactant may be from about 1.1:1 to about 30:1 or higher. The products formed are primarily the aldehyde corresponding to the carboxylic reactant, water or an alcohol if the carboxylic reactant is an ester and minor proportions of by-products.

Any suitable means may be used to introduce the carboxyl-containing reactant. In particular, in the case of benzoic acid which is a solid at room temperature, it is preferred to preheat the storage and inlet system to provide continuous addition of liquid carboxylic reactant to the hydrogen stream. Alternatively, the benzoic acid may be first dissolved in methanol solvent before introduction into the reactor. Since the presence of methanol in the reaction is likely to lead to production of by-products it is preferred to operate without the use of methanol.

Contact of the reactant mixture with the catalyst bed may be continued for a sufficient time to allow substantially complete reduction of the carboxylic reactant to occur. In a batch process the reactor containing catalyst and reactants may be heated for a sufficient time before cooling and recovery of products. Alternatively, the reactant mixture may be recirculated in a closed system through the reactor and back by an external return for a sufficient period to allow the reaction to proceed to substantial completion. In a continuous process the rate of hydrogen flow and reactor size may be varied to control the duration of reaction.

Catalyst regeneration is occasionally required in order to cleanse the catalyst surface of accumulated organic materials formed during the reduction process. The catalyst is easily regenerated by heating in the presence of an oxygen-containing gas for a time sufficient to restore catalytic activity. Such a regeneration is well-known to the skilled artisan and need not be described in further detail.

SPECIFIC EMBODIMENTS

The following examples are provided as further illustrative of the invented process and are not to be construed as limiting.

As illustrative of catalyst manufacture about 35 g of thorium nitrate tetrahydrate is dissolved in 11 ml of hot water. Fifty $cm^3$ of $\alpha$-$Al_2O_3$ ($-10+16$ screen) is added to the solution and thoroughly mixed. Excess water is removed by evaporation until the pellets are dry to the appearance. Concentrated $NH_4OH$ (22 ml) is added and the mixture digested for several minutes. The pellets are then rinsed with five 100 ml portions of water.

After drying at room temperature the catalyst is roasted in a furnace the temperature being raised 25° C./hr until a temperature of 450° C. is reached. After roasting at 450° C. for one hour the catalyst is removed and ready for use.

About 12 cc of the catalyst is loaded into a 3/8" diameter stainless steel pipe reactor. The reactor is immersed in a molten salt bath maintained at about 360° C. Nitrogen is passed through the reactor to sweep out air.

EXAMPLE 1

Methyl benzoate reduction

Methyl benzoate was reduced by injecting small samples into a preheated hydrogen stream which was then passed over catalysts prepared according to the above procedure. The temperature and other parameters of the reaction are illustrated by the following table.

TABLE I

| Catalyst (wt % metal oxide) | $H_2$ GHSV* (l/1 hr) | LHSV** g/l hr | Length of run (hrs.) | Reaction Temp. (°C.) | Conversion (mole %) | Aldehyde Selectivity (mole %) |
|---|---|---|---|---|---|---|
| Yttrium Oxide (22.2) | 625 | 92.4 | 18.0 | 370 | 48.3 | 88.0 |
| Cerium Oxide (22.7) | 625 | 88.8 | 20.5 | 364 | 89.8 | 63.1 |
| Praseodymium Oxide (22.3) | 625 | 94.1 | 21.0 | 372 | 23.0 | 90.7 |
| Thorium Oxide (14.2) | 500 | 86.6 | 19.7 | 360 | 18.8 | 74.1 |
| Zirconium Oxide (98.0) | 625 | 83.5 | 19.5 | 365 | 98.6 | 64.7 |
| Uranium Oxide (25.6) | 600 | 96.3 | 19.0 | 364 | 24.3 | 59.6 |

*GHSV = Gas-hourly space velocity = Liters of hydrogen per liter of catalyst per hour at 25° C. and 1 atmosphere.
**LHSV = Liquid-hourly space velocity = grams of methyl benzoate per liter of catalyst per hour.

EXAMPLE 2

Benzoic acid reduction

The procedure employed in Example 1 was repeated except that benzoic acid preheated to a liquid was injected continuously into the preheated hydrogen stream. The results of the reduction are contained in Table II.

TABLE II

| Catalyst (wt % metal oxide) | $H_2$ GHSV (l/1 hr) | LHSV g/l hr | Length of run (hrs.) | Reaction Temp. (°C.) | Conversion (mole %) | Aldehyde Selectivity (mole %) |
|---|---|---|---|---|---|---|
| Yttrium Oxide (21.0) | 625 | 70.0 | 18.8 | 440 | 91.0 | 96.2 |
| Cerium Oxide (30.7) | 625 | 77.5 | 21.7 | 425 | 100.0 | 82.4 |
| Zirconium* Oxide (98.0) | 625 | 75.0 | 21.7 | 430 | 97.7 | 91.6 |
| Praseo-** dymium Oxide (~100.0) | 625 | 131.3 | 21.8 | 432 | 37.0 | 39.0 |

*Compressed pellets commercially available from Harshaw Chemical Company.
**Compressed pellets unsupported.

EXAMPLE 3

Reduction of Other Acids and Esters

The proceudre in Example 1 was repeated except that esters and acids other than benzoic acid or methyl benzoate were reduced. The catalyst used in these reductions was 21.0 percent yttrium oxide supported on $\alpha$-alumina. The results of the reduction are contained in Table III.

TABLE III

| Organic Feed | H$_2$ GHSV (l/l hr) | LHSV g/l hr | Length of run (hrs.) | Reaction Temp. (°C.) | Conversion (mole %) | Aldehyde Selectivity (mole %) |
| --- | --- | --- | --- | --- | --- | --- |
| p-Methyl Anisate | 625 | 94.4 | 15.6 | 375 | 93.0 | 31.0 |
| Methyl Isobutyrate | 625 | 119.6 | 17.3 | 380 | 39.0 | 66.0 |
| Methyl Trimethylacetate | 625 | 86.0 | 18.8 | 375 | 30.0 | 89.0 |
| Ethyl Benzoate | 625 | 105.5 | 20.8 | 375 | 18.4 | 74.0 |
| p-Toluic Acid | 625 | 190.2 | 18.6 | 446 | 17.0 | 32.0 |

EXAMPLE 4

A hydrogen stream of 417 l/l-hour and a molten 3-chlorobenzoic acid stream of 64.3 g/l-hr were combined in a preheated mixing zone and the mixture was passed through a bed of 98 percent zirconium oxide/2 percent aluminum oxide pellets held at 427° C. After 4 hours the run was terminated. The conversion was 85 percent and the selectivity to 3-chlorobenzaldehyde was 53.7 percent.

What is claimed is:

1. In the catalytic vapor phase reduction wherein a monocarboxylic acid or ester thereof capable of being reduced to the corresponding aldehyde is contacted with hydrogen in the presence of a catalyst at a temperature and for a time sufficient to produce an aldehyde, the improvement wherein the catalyst comprises the oxide of yttrium, cerium, praseodymium, zirconium, or uranium.

2. The improvement of claim 1 wherein the catalyst comprises the oxide of yttrium or zirconium.

3. The improvement of claim 1 wherein the catalyst is deposited on an inert supportive means.

4. The improvement of claim 3 wherein the inert supportive means is alumina.

5. The improvement according to claim 1 wherein the carboxylic acid or ester is:
   (1) a $C_{1-12}$ monocarboxylic acid selected from
      (i) aliphatic acids having zero or one α hydrogen; and
      (ii) benzoic acid or alkyl-, alkoxy-, hydroxy- or halosubstituted derivatives thereof; or
   (2) phenyl and $C_{1-6}$ alkyl esters and diesters of (1).

6. The improvement according to claim 1 wherein the monocarboxylic acid or ester is selected from benzoic and alkyl- or halo-substituted benzoic acids, di- and trialkyl-substituted acetic acids, and phenyl or $C_{1-6}$ alkyl esters thereof.

7. The improvement according to claim 1 wherein the monocarboxylic acid of ester is benzoic acid or $C_{1-6}$ alkyl benzoate.

* * * * *

UNITED STATES PATENT AND TRADEMARK OFFICE
CERTIFICATE OF CORRECTION

PATENT NO. : 4,328,373
DATED : May 4, 1982
INVENTOR(S) : Edwin J. Strojny

It is certified that error appears in the above—identified patent and that said Letters Patent is hereby corrected as shown below:

Column 1, line 26, "been disclosed. p It is" should read -- been disclosed. It is --.

Column 4, Example 3, line 63, "The proceudre in" should read -- The procedure in --.

Column 6, line 29, "acid of ester" should read -- acid or ester --.

Signed and Sealed this

Eighth Day of February 1983

[SEAL]

Attest:

GERALD J. MOSSINGHOFF

Attesting Officer

Commissioner of Patents and Trademarks